United States Patent
Leflaive et al.

(10) Patent No.: US 7,838,714 B2
(45) Date of Patent: *Nov. 23, 2010

(54) PROCESS AND DEVICE FOR IMPROVED SEPARATION OF METAXYLENE IN A SIMULATED MOVING BED

(75) Inventors: Philibert Leflaive, Mions (FR); Luc Wolff, Chaponnay (FR); Damien Leinekugel Le Cocq, Lyons (FR)

(73) Assignee: IFP Energies Nouvelles, Rueil Malmaison Cedex (FR)

( * ) Notice: Subject to any disclaimer, the term of this patent is extended or adjusted under 35 U.S.C. 154(b) by 175 days.

This patent is subject to a terminal disclaimer.

(21) Appl. No.: 12/181,525

(22) Filed: Jul. 29, 2008

(65) Prior Publication Data
US 2009/0036726 A1   Feb. 5, 2009

(30) Foreign Application Priority Data
Jul. 30, 2007 (FR) .................................. 07 05616

(51) Int. Cl.
*C07C 7/12* (2006.01)

(52) U.S. Cl. ............... 585/828; 585/820; 585/825; 585/826; 585/827

(58) Field of Classification Search ............ 585/820, 585/828
See application file for complete search history.

(56) References Cited

U.S. PATENT DOCUMENTS

| | | | |
|---|---|---|---|
| 5,900,523 A | 5/1999 | Kulprathipanja | |
| 6,838,588 B2 * | 1/2005 | Leflaive et al. | 585/828 |
| 6,841,714 B2 * | 1/2005 | Leflaive et al. | 585/828 |
| 7,390,412 B2 * | 6/2008 | Pavone | 210/659 |
| 7,473,368 B2 * | 1/2009 | Hotier | 210/659 |
| 2002/0055665 A1 | 5/2002 | Pavone et al. | |
| 2002/0143223 A1 | 10/2002 | Leflaive et al. | |
| 2004/0256323 A1 | 12/2004 | Pavone | |
| 2010/0048973 A1 * | 2/2010 | Decoodt et al. | 585/822 |

FOREIGN PATENT DOCUMENTS

| | | |
|---|---|---|
| EP | 1 245 552 A | 10/2002 |
| FR | 2 808 270 A | 11/2001 |
| FR | 2 856 313 A | 12/2004 |
| FR | 0 705 616 R | 3/2008 |

* cited by examiner

*Primary Examiner*—Tam M Nguyen
(74) *Attorney, Agent, or Firm*—Millen, White, Zelano & Branigan, P.C.

(57) ABSTRACT

Process for separation of metaxylene, with at least 99% by weight of purity of an aromatic feedstock F, in a single adsorption stage in a simulated moving bed in an SMB device that comprises 12, 13 or 15 adsorbent beds with different numbers of beds being employed in zone 1 between the supply of the desorbent D and the draw-off of the extract E; zone 2 between the draw-off of the extract E and the supply of the feedstock F; zone 3 between the supply of the feedstock and the draw-off of the raffinate R; and zone 4 between the draw-off of the raffinate R and the supply of the desorbent D whereby the process is carried out according to a configuration of zones (a, b, c, d), whereby a, b, c, and d represent the number of adsorbent beds that operate respectively in zones 1, 2, 3, 4 in which there is used:
  Either an SMB of 12 adsorbent beds operating according to the configuration (2, 5, 3, 2),
  Or an SMB of 13 adsorbent beds operating according to the configuration (2, 5, 4, 2),
  Or an SMB of 15 adsorbent beds operating according to the configuration (2, 6, 4, 3).

8 Claims, 1 Drawing Sheet

[Key to Fig. 1:]

Rendement (%) – Yield (%)

Nombre de lits = Number of Beds

PROCESS AND DEVICE FOR IMPROVED SEPARATION OF METAXYLENE IN A SIMULATED MOVING BED

CROSS-REFERENCE TO RELATED APPLICATION

This application is related to concurrently filed application attorney docket number PET-2481, entitled "Process And Device For Improved Separation Of Paraxylene In A Simulated Moving Bed", by Philibert LEFLAIVE, Damien LEINEKUGEL-LE-COCQ, and Luc WOLFF, claiming priority of French Application Ser. No. 07/05.615 filed Jul. 30, 2007, said cross-referenced application being incorporated by reference herein.

FIELD OF THE INVENTION

The invention relates to the field of the separation of metaxylene (MX) from an aromatic hydrocarbon feedstock essentially with 8 carbon atoms. "Essentially" is defined as the fact that the feedstock to be treated contains at least 95% xylenes, and preferably at least 97% xylenes.

This type of feedstock cannot be easily separated by distillation. A family of adsorption processes and associated devices, known under the name of "chromatographic" or "simulated moving bed" or "simulated counter-current" or "simulated co-current" processes or separation devices, which we will designate below by the name of "SMB" for "Simulated Moving Bed", is then used.

The SMB separation of the high-purity, typically with at least 99% by weight metaxylene is carried out industrially in SMB devices that comprise 24 adsorbent beds. A raffinate that is high in ethylbenzene (EB), orthoxylene (OX) and optionally paraxylene (PX), often recycled with SMB after isomerization, is also produced.

The invention relates to an SMB separation process that makes it possible to obtain—in a single stage—MX with a commercial purity of more than 99% and typically 99.5% by weight, in less complex SMB devices than those of the prior art, in particular with a reduced number of adsorbent beds and specific configurations of the adsorption/desorption zones.

PRIOR ART

The SMB chromatographic separation is well known in the prior art. As a general rule, a simulated moving bed comprises at least three chromatographic zones and optionally four or five, whereby each of these zones consists of at least one bed or a column portion and is located between two successive supply or draw-off points. Typically, at least one feedstock F to be fractionated and one desorbent D (sometimes called eluant) are supplied, and at least one raffinate R and one extract E are drawn off. The supply and draw-off points are modified over time, typically offset toward the bottom of a bed in a synchronous manner.

By definition, each of the operating zones is designated by a number:

Zone 1=Zone for desorption of the desired product (here, metaxylene contained in the extract) located between the injection of the desorbent D and the sampling of extract E;

Zone 2=Zone for desorption of the compounds of the raffinate, located between the sampling of the extract E and the injection of the feedstock to be fractionated F;

Zone 3=Zone for adsorption of the desired product (metaxylene), located between the injection of the feedstock and the draw-off of the raffinate R, and;

Zone 4 located between the draw-off of the raffinate and the injection of the desorbent.

The process for separation in an SMB device therefore operates according to a configuration (a, b, c, d) with:

a=Number of adsorbent beds operating in zone 1;
b=Number of adsorbent beds operating in zone 2;
c=Number of adsorbent beds operating in zone 3;
d=Number of adsorbent beds operating in zone 4.

In an in-depth way, the prior art describes various devices and processes that make it possible to carry out the separation of feedstocks in a simulated moving bed. It is possible to cite in particular the patents U.S. Pat. Nos. 2,985,589, 3,214,247, 3,268,605, 3,592,612, 4,614,204, 4,378,292, 5,200,075, and 5,316,821. These patents also describe in detail the operation of an SMB.

The SMB devices typically comprise at least one column (and often two), adsorbent beds $A_i$ that are located in this column, separated by plates $P_i$ with chamber(s) $C_i$ for distributing and/or extracting fluids in or from various adsorbent beds, and controlled means for sequential distribution and extraction of fluids.

These controlled means for distributing and extracting fluids of an SMB are typically one of the following two major types of technology:

Either, for each plate, a number of all-or-nothing (on-off) controlled valves for the supply or the draw-off of fluids, whereby these valves are typically located in the immediate vicinity of the corresponding plate and comprise in particular, for each plate $P_i$, at least four all-or-nothing controlled two-way valves for respectively the supply of fluids F and D and the draw-off of fluids E and R.

Or a multiple-path rotary valve for the supply or the draw-off of fluids on the set of plates.

The separation of the metaxylene of aromatic fractions is typically carried out by SMB separation that makes it possible to obtain high-purity MX directly, typically of 99.0% by weight or more. This process also makes it possible to obtain a raffinate that is high in ethylbenzene, orthoxylene and optionally paraxylene (if the feedstock contains them), often recycled in the SMB after isomerization. The SMB units of this type typically operate with 24 adsorbent beds, because it is considered that this number of adsorbent beds, which is also the number of beds used for the SMB separation of paraxylene, is necessary to obtain the MX at the high purity that is desired, more than 99.0% and typically at least 99.5% by weight, or at least to obtain this purity with an acceptable yield of MX.

The higher the number of beds, the closer it is possible to come to an actual fluid/adsorbent counter-current, which is a continuous process, equivalent to an SMB process with an infinite number of beds. Thus, for the high-purity MX, it is assumed that 24 beds are necessary to obtain the desired purity and an acceptable yield.

Such an SMB separation unit is operated in general at a temperature of between 20° C. and 250° C., preferably between 90° C. and 210° C., and more preferably between 140° C. and 200° C., and under a pressure of between the bubble pressure of the xylenes at the operating temperature and 2 MPa. The desorbent that is used in the SMB unit is generally toluene. The volumetric ratio of the desorbent to the feedstock in the SMB unit is typically between 0.5 and 6, and preferably between 1.5 and 4.5.

It will also be possible to refer to the above-mentioned patent applications or patents or the following: U.S. Pat. Nos. 5,900,523; 4,306,107; 4,326,092.

SIMPLIFIED DESCRIPTION OF THE INVENTION

The invention relates to an SMB separation process that makes it possible to obtain—in a single stage—MX with a high purity of more than 99% and typically 99.5% by weight, in SMB devices that are less complex than those of the prior art, in particular with a reduced number of adsorbent beds. It has actually been discovered that contrary to what was considered previously, obtaining a high purity by SMB in a direct path was possible with a limited number of adsorbent beds, provided that a double selection was simultaneously carried out:
  Specific number of adsorbent beds,
  Specific configuration of zones (a, b, c, d).

More specifically, it was found that it was possible to obtain unexpected performance levels that are industrially advantageous by using in combination:
  12 beds in configuration (2, 5, 3, 2), or else:
  13 beds in configuration (2, 5, 4, 2), or else:
  15 beds in configuration (2, 6, 4, 3).

DETAILED DESCRIPTION OF THE INVENTION

The invention therefore proposes a process for separating metaxylene with a purity of at least 99.0% by weight, and preferably at least 99.5% by weight, from a feedstock F of aromatic hydrocarbons having essentially 8 carbon atoms, by direct separation into a single stage of adsorption in a simulated moving bed in an SMB device with at least one column that comprises a number of adsorbent beds that are separated by distribution/extraction plates $P_i$, in which at least the feedstock F and one desorbent D are fed into this device, and at least one extract E that is high in metaxylene and at least one raffinate R are drawn off, whereby the supply and draw-off points are changed over time with a switching time T and determine a number of operating zones of the SMB, and in particular the following primary zones:
  A zone 1 for desorption of metaxylene that is located between the supply of the desorbent D and the draw-off of the extract E;
  A zone 2 for desorption of the compounds of the raffinate, located between the draw-off of the extract E and the supply of the feedstock F;
  A zone 3 for the adsorption of at least the metaxylene, located between the supply of the feedstock and the draw-off of the raffinate R;
  A zone 4 that is located between the draw-off of the raffinate R and the supply of the desorbent D, whereby the process is carried out according to a configuration of zones (a, b, c, d) with:
  a=Number of adsorbent beds operating in zone 1;
  b=Number of adsorbent beds operating in zone 2;
  c=Number of adsorbent beds operating in zone 3;
  d=Number of adsorbent beds operating in zone 4, whereby the process implements one of the following options:
  Either an SMB of 12 adsorbent beds operating according to the configuration (2, 5, 3, 2) is used,
  Or an SMB of 13 adsorbent beds operating according to the configuration (2, 5, 4, 2) is used,
  Or an SMB of 15 adsorbent beds operating according to the configuration (2, 6, 4, 3) is used.

The use of these double selections makes it possible to obtain results that are superior to those of all of the other possible combinations for an identical or close number of adsorbent beds. The prior art had considered that obtaining a very high purity required a process that was close to a simulated actual countercurrent (continuous process that is equivalent to an SMB process with an infinite number of beds), and therefore a high number of beds: typically 24. It is thought that certain configurations with a reduced number of beds have a distribution of zones that lends itself particularly well to separation, and that the latter leads to unsuspected performance levels, with an SMB with a reduced number of beds, which is particularly economical (fewer controlled valves, fewer distribution/extraction systems, fewer pipes).

Preferably, the process is implemented with a desorbent that belongs to the group that is formed by toluene and tetralin. It is possible in particular to use toluene.

Preferably, for a given SMB, the operation is performed with conditions (in particular flow of feedstock and flow of solvent) that make it possible to obtain a purity of 99.5% by weight, i.e., the typically desired purity.

BRIEF DESCRIPTION OF DRAWINGS

The FIGURE is a graph which shows the yield of metaxylene based on the number of adsorbent beds for various zone configurations in an SMB operating with toluene as a desorbent.

The interpretation of this FIGURE will be elaborated in Example 2 below.

EXAMPLES

Figure 1:
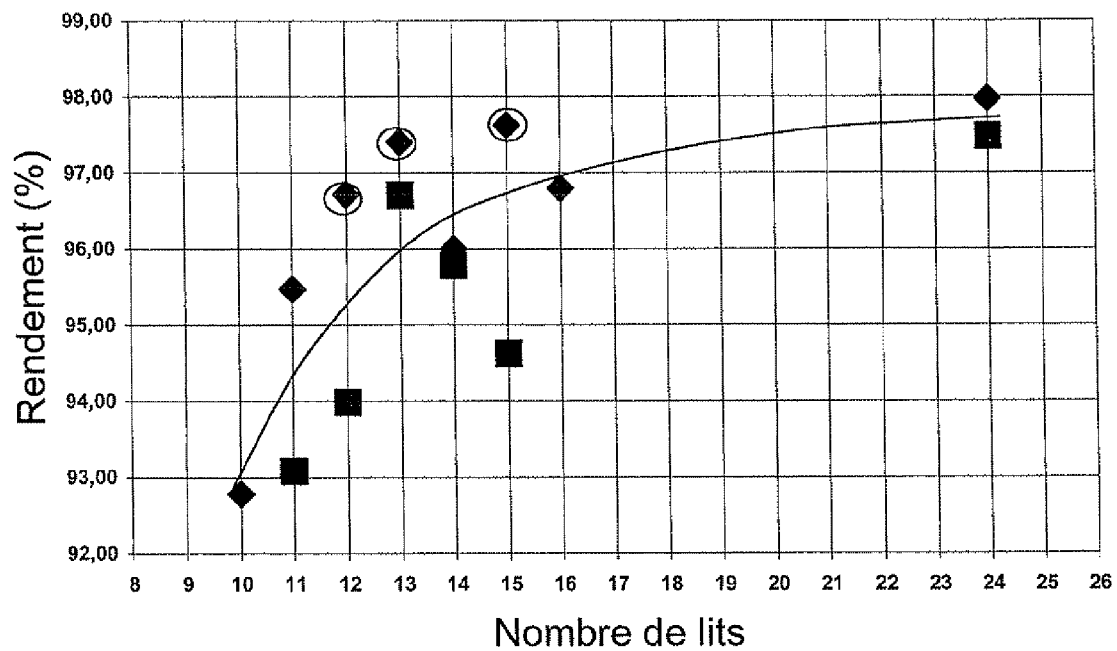

The invention will be better understood from reading the following non-limitation examples, in which:
  Example 1 is representative of the prior art for obtaining high-purity toluene. A typical SMB device with 24 adsorbent beds is used, with toluene as a desorbent.
  Example 2 describes the performance levels of an SMB device that has the same overall adsorbent volume as that of Example 1, but distributed between a smaller number of beds, according to various zone configurations and also using toluene as a desorbent. Certain bed number/zone configuration combinations are in accordance with the invention.

Comparative Example 1 According to the Prior Art

Metaxylene is separated from an aromatic feedstock with 8 carbon atoms on an SMB device in a simulated moving bed that is equipped with 24 adsorbent beds and that uses toluene as a desorbent.

This SMB device comprises 24 adsorbent beds with a 1.1 m height and a $3.5 \times 10^{-4}$ m$^2$ internal section, with an injection of feedstock, an injection of desorbent, a draw-off of extract, and a draw-off of raffinate. The effective zone configuration is (4, 10, 6, 4), or:
  4 beds in zone 1;
  10 beds in zone 2;
  6 beds in zone 3;
  4 beds in zone 4.

The adsorbent that is used is an NaY-type zeolite, and the desorbent is toluene. The temperature is 160° C., and the pressure is 1.0 MPa.

The feedstock F consists of 20% PX, 22% OX, 48% MX, and 5% EB. The switching time that is used is 89.4 seconds. The liquid flow rates in the various zones are as follows:

4.03 cm$^3$.s$^{-1}$ in zone 1;
3.12 cm$^3$.s$^{-1}$ in zone 2;
3.38 cm$^3$.s$^{-1}$ in zone 3;
2.82 cm$^3$.s$^{-1}$ in zone 4.

An MX purity in the extract of 99.5% by weight and an MX yield (ratio of the MX of the extract to the MX of the feedstock) of 97.97% by weight are then obtained by simulation.

Example 2

The MX is separated from the same feedstock F in an SMB device that comprises an adsorber that has the same diameter and the same overall volume of the same adsorbent as the one of Example 1, but distributed between a number n of beds that is less than 24, according to various zone configurations. For this purpose, adsorbent beds with a height $L_n = 24/n \times L_{24}$ are considered, with:

$L_n$=bed height in the SMB with n beds.
$L_{24}$=bed height in the SMB with 24 beds.
This SMB also uses toluene as a desorbent.

All of the tests are carried out with an isopurity of 99.5% by weight, which is the purity that is obtained in Example 1, isoflow of desorbent D and feedstock F relative to Example 1.

In addition, so as to preserve the ratio between the liquid flow rates and the equivalent solid flow rate in each zone, the switching time $T_n$ of the same factor as the height of the beds is adapted relative to the switching time $T_{24}$ of the SMB with 24 beds: $T_n = 24/n \times T_{24}$. This value is then slightly corrected so as to make it isopure and therefore to allow a comparison of the different systems based on the yields.

The yield obtained in MX for different numbers of beds, located between 10 and 16, and with various zone configurations, was tested by simulation.

FIG. 1 shows (in diamond-shaped dots) the curve of the yield that is obtained for each number of beds and for the best possible zone configuration. A mean curve was plotted in dotted lines, and the noteworthy yield dots were circled. Certain additional dots (square-shaped dots), corresponding to other non-optimum configurations, were also shown.

Surprisingly enough, it is seen that the curve of evolution of the yield with the number of beds exhibits 3 optimum configurations: the SMB with 12, 13 and 15 beds, which become detached from the mean curve, for their optimum configuration. The dot corresponding to 11 beds is also above the curve, but the yield that is obtained is still only moderate. It is also seen that the other configurations lead to considerably lower yields. This is reflected in Tables 1, 2 and 3 below. Only the best configurations that make it possible to obtain the desired degree of purity are mentioned.

TABLE 1

Study of the Influence of the Zone Configuration in the 15-Bed Case.

| Configuration | Yield of Metaxylene |
| --- | --- |
| 2, 6, 4, 3 | 97.62% |
| 3, 6, 3, 3 | 94.62% |
| 3, 7, 3, 2 | 92.35% |

TABLE 2

Study of the Influence of the Zone Configuration in the 13-Bed Case.

| Configuration | Yield of Metaxylene |
| --- | --- |
| 2, 5, 4, 2 | 97.40% |
| 2, 6, 3, 2 | 96.70% |
| 2, 5, 3, 3 | 95.97% |

TABLE 3

Study of the Influence of the Zone Configuration in the 12-Bed Case.

| Configuration | Yield of Metaxylene |
| --- | --- |
| 2, 5, 3, 2 | 96.71% |
| 2, 4, 3, 3 | 93.98% |

The physical interpretation of these results is not obvious. It is thought that the association of a particular number of beds with a particular zone configuration may prove quite superior to other possibilities for the effectiveness of separation and yield. The importance of this double selection: number of beds/zone configurations had not been taken into consideration in the prior art of the separation of the MX, which, moreover, considers that obtaining high-purity MX requires 24 beds.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding French application No. 07/05.616, filed Jul. 30, 2007 are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

In the following claims, the numerical values of a, b, c and d are set forth in parenthesis, it being understood for example that a configuration of (2, 5, 3, 2) means that in zone 1, there are 2 adsorbent beds, in zone 2, there are 5 adsorbent beds, in zone 3, there are 3 adsorbent beds, and in zone 4, there are 2 adsorbent beds.

The invention claimed is:

1. A process for separating metaxylene with a purity of at least 99% by weight from a feedstock F of aromatic hydrocarbons having essentially 8 carbon atoms by direct separation into a single stage of adsorption in a simulated moving bed in a simulated moving bed (SMB) absorption device with at least one column that comprises a number of adsorbent beds that are separated by distribution/extraction plates $P_i$, in which at least one feedstock F and one desorbent D are fed into this device, and at least one extract E that is high in paraxylene and at least one raffinate R are drawn off, whereby the supply and draw-off points are changed over time with a switching time T providing a number of operating zones of the SMB, the following primary operating zones of the SMB:
- a zone 1 for desorption of the metaxylene that is located between the supply of the desorbent D and the draw-off of the extract E;
- a zone 2 for desorption of the compounds of the raffinate, located between the draw-off of the extract E and the supply of the feedstock F;
- a zone 3 for the adsorption of at least metaxylene, located between the supply of the feedstock and the draw-off of the raffinate R;
- a zone 4 that is located between the draw-off of the raffinate R and the supply of the desorbent D, and conducting the process according to a predetermined configuration of zones (a, b, c, d) with:
- a=number of adsorbent beds operating in zone 1;
- b=number of adsorbent beds operating in zone 2;
- c=number of adsorbent beds operating in zone 3;
- d=number of adsorbent beds operating in zone 4;

said predetermined configuration being one of the following:
- An SMB of 12 adsorbent beds operating according to configuration (2, 5, 3, 2),
- or an SMB of 13 adsorbent beds operating according to configuration (2, 5, 4, 2),
- or an SMB of 15 adsorbent beds operating according to configuration (2, 6, 4, 3).

2. A process according to claim 1, conducted with an SMB of 12 adsorbent beds operating according to configuration (2, 5, 3, 2).

3. A process according to claim 1, conducted with an SMB of 13 adsorbent beds operating according to configuration (2, 5, 4, 2).

4. A process according to claim 1, conducted with an SMB of 15 adsorbent beds operating according to configuration (2, 6, 4, 3).

5. A process according to claim 1, in which the desorbent comprises toluene or tetralin.

6. A process according to claim 5, in which the desorbent is toluene.

7. A process according to claim 1, in which the operation is conducted with a sufficient feedstock flow rate coupled with a sufficient solvent flow rate to result in a metaxylene purity of 99.5% by weight.

8. A process according to claim 7, wherein the adsorbent is a NaY zeolite, the desorbent is toluene and process is conducted at between 20 and 250° C., a pressure between the bubble pressure of xylenes at the operating temperature and 2 MPa are a volumetric ratio of desorbent to feedstock of between 0.5 and 6.

* * * * *